United States Patent [19]

Jaekel

[11] Patent Number: 5,470,988

[45] Date of Patent: Nov. 28, 1995

[54] PROCESS FOR THE PREPARATION OF PURIFIED PHTHALIMIDOALKANECARBOXYLIC ACIDS

[75] Inventor: Frank Jaekel, Bad Soden/Ts, Germany

[73] Assignee: Hoechst Aktiengesellschaft, Frankfurt, Germany

[21] Appl. No.: 181,575

[22] Filed: Jan. 13, 1994

[30] Foreign Application Priority Data

Jan. 16, 1993 [DE] Germany .................. 43 01. 024.5

[51] Int. Cl.$^6$ ................................ C07D 209/48
[52] U.S. Cl. ........................................ 548/479
[58] Field of Search ............................ 548/479

[56] References Cited

U.S. PATENT DOCUMENTS 3,210,313  10/1965  Taub .................................. 548/473
5,061,807  10/1991  Gethöffer et al. .................. 548/473
5,310,934   5/1994  Calvallotti et al. ................. 548/479

FOREIGN PATENT DOCUMENTS 0349940  1/1990  European Pat. Off. .

*Primary Examiner*—Jacqueline Haley
*Attorney, Agent, or Firm*—Connolly & Hutz

[57] ABSTRACT

Process for the preparation of purified phthalimidoalkanecarboxylic acids

The present invention relates to a process for the preparation of purified phthalimidoalkanecarboxylic acids which are contaminated with phthalic acid, lactam and/or water, including the following measures:

a) fusing the contaminated phthalimidoalkanecarboxylic acid, b) holding the melt for a period and at a temperature sufficient for the impurities to have substantially departed from the melt and c) cooling the purified product melt.

21 Claims, No Drawings

PROCESS FOR THE PREPARATION OF PURIFIED PHTHALIMIDOALKANECARBOXYLIC ACIDS

DESCRIPTION

Process for the preparation of purified phthalimidoalkanecarboxylic acids

Phthalimidoalkanecarboxylic acids serve as starting materials for the corresponding peracids which are used as oxidizing agents in cleaning agents, bleaches, disinfectants and oxidizing agents.

The phthalimidoalkanepercarboxylic acids, apart from good bleaching properties, are also distinguished by good storage stability, which is achieved even without additions (phlegmatization) or dilution with inert substances, such as phosphine oxide/sodium sulfate, boric acid or magnesium sulfate. Because of this property profile, phthalimidoalkanepercarboxylic acids are gaining an increasing importance as bleaching systems in washing agents.

In the specialist literature, numerous methods are known for the preparation of phthalimidoalkanecarboxylic acids.

In Chem. Ber. Vol. 46, page 3158 (1913), the preparation is described of phthalimidoalkanecarboxylic acids by condensation of phthalic anhydride and amino acids. However, the high prices of the amino acids are an obstacle to industrial realization.

J. Am. Chem. Soc. 70, 2115 (1948) and J. Org. Chem. 24, 2062 (1959) disclose the preparation of 6-phthalimidohexanoic acid by heating ε-caprolactam with phthalic anhydride to a temperature of 180°–195° C. The product obtained is isolated either by distillation or recrystallization in yields between 65 and 80 %. In this process, although easily available starting materials can be employed, the yields are unsatisfactory for an industrial large-scale product.

Japanese Patent No. Sho-46/21710 (date of grant: 19 Jun. 1971) discloses the preparation of 4-phthalimidobutanoic acid from phthalic anhydride and pyrrolidone in the presence of 5 to 15 % of water at temperatures of 180° C. and reaction times of 5 hours. In order to obtain a sufficiently pure product, it is necessary to recrystallize the isolated crude product from methanol. The yield is 86 %.

EP-A-0,349,940 mentions a process for the preparation of phthalimidoalkanecarboxylic acids by reaction of phthalic anhydride and lactams, e.g. ε-caprolactam, in the presence of water at a pressure of 1 to 30 bar, temperatures of 100° to 250° C. and reaction times of 5 to 20 hours.

In the above described processes, the phthalimidoalkanecarboxylic acids, before their purification, contain impurities of phthalic acid, amino acid or lactam and/or water.

When phthalimidoalkanecarboxylic acids are used as starting materials for the corresponding phthalimidoalkanepercarboxylic acids, such impurities are undesirable for several reasons. The phthalimidoalkanecarboxylic acids are conventionally oxidized by reaction with hydrogen peroxide in the presence of a strong acid to form the corresponding peracids. When phthalic acid is present, this reacts to form monoperoxophthalic acid which, in contrast to the phthalimidoalkanepercarboxylic acids, has only low storage stability and must usually be phlegmatized or converted into the magnesium salt (cf. EP-A-0,105,689). Phthalimidoalkanepercarboxylic acids which are contaminated by unphlegmatized monoperoxophthalic acid would lose some of their good storage stability.

In EP-A-0,490,409, a process is described for the preparation of arylimidoalkanepercarboxylic acids, in which arylimidocarboxylic acids are dissolved in methylene chloride or chloroform and are continuously oxidized by hydrogen peroxide in the presence of a strong acid to give the corresponding percarboxylic acids. For the optimal execution of this process, it is imperative in this process that the arylimidocarboxylic acids are completely dissolved in methylene chloride or chloroform. Since neither phthalic acid, water nor amino acid or lactam dissolve in this solvent, the arylimidocarboxylic acids used must be free from these impurities to the greatest possible extent, if it is not desired to separate off the solid or liquid impurities by additional purification steps—such as filtration of phase separation.

The object of the present invention is to provide a process for the purification of phthalimidoalkanecarboxylic acids which enables the impurities of phthalic acid, lactam, and/or water which are present to be removed to the greatest possible extent.

The invention relates to a process for the preparation of purified phthalimidoalkanecarboxylic acids which are contaminated with phthalic acid, lactam and/or water, including the following measures:

a) fusing the contaminated phthalimidoalkanecarboxylic acid, b) holding the melt for a period and at a temperature sufficient for the impurities to have substantially departed from the melt and c) cooling the purified product melt.

The unpurified phthalimidoalkanecarboxylic acids used are generally products of known preparation processes. These contaminated phthalimidocarboxylic acids conventionally contain the following impurities:

1.5–10% by weight of phthalic acid,
0.5–10% by weight of lactam:
1.0–20 % by weight of water.

For carrying out the process according to the invention there are various embodiments.

The contaminated phthalimidoalkanecarboxylic acid is first melted in suitable equipment, e.g. a heatable stirred tank. The fusion is preferably carried out under treatment with an inert gas., such as argon, nitrogen or carbon dioxide. The gas treatment can be carried out in various ways. It is thus conceivable that the gas is passed over the melt, is injected into the melt with the aid of an apparatus (e.g. "lance") or is introduced into the stirred tank in another manner known to those skilled in the art. The melt temperature is preferably between 10° and 200° C. particularly preferably 130° to 170° C.

The inert gas pressure in the equipment is then reduced by applying a vacuum. The inert gas pressure in the equipment is usually 0.1 to 300mbar, preferably 1 to 140 mbar, particulary preferably 4 to 95mbar. The period for which the vacuum is applied is dependent on the desired purity of the phthalimidoalkanecarboxylic acid and the temperature of the crude product melt and is generally up to 5 hours. It has been shown that, at a melt temperature of 140° C. and a vacuum of 105 mbar, even after less than 3 hours, the content of phthalic acid, starting from 1.26% by weight, decreases to less than 0.5% by weight. Under these conditions, the water content falls from 4.10% by weight to below 0.1% by weight even after half an hour. It is generally true that higher temperatures or a lower pressure shorten the period required or increase the degree of purity of the product.

In a further embodiment of the process according to the invention, the crude product is treated in suitable equipment, e.g. a pressure-stable heatable stirred tank, after evacuation of the apparatus, with an inert gas and is melted in the closed equipment. The super atmospheric pressure resulting during heating is released from time to time. After the depressurization, inert gas is passed again into the apparatus, the apparatus is sealed pressure-tightly and, after a super atmospheric pressure is established, is again depressurized. This process is repeated until super atmospheric pressure no longer forms.

However, the corresponding continuous process is preferred to this batchwise process.

In the continuous process, the crude product is treated with an inert gas and melted in suitable equipment, e.g. a pressure-stable heatable stirred tank. The gas treatment of the melt is preferably carried out bypassing an inert gas stream over it, the flow rate of the inert gas stream being conventionally 0.1 to 50 l/h, preferably 1 to 30 l/h, particularly preferably 2 to 20 l/h. The gas stream can be passed into the apparatus at atmospheric pressure or alternatively at a slightly reduced pressure, preferably in the range of 500–800 mbar. Depending on the contamination of the crude product, the reduced pressure can also be lower. The period during which the inert gas stream is passed over the product melt is normally 0.1 to 6 hours,, preferably 0.3 to 3 hours, particularly preferably 0.5 to 1.5 hours. This period is dependent on the required purity, the product melt temperature and the reduced pressure applied.

Subsequently to the above-described measures b), the melt is cooled and the product is fed to further processing, e.g. fabrication. The melt is conventionally cooled to the solidification point. Furthermore, it is conceivable to cool the melt to immediately above the solidification point, in order on the one hand to be able to remove it easily from the reaction vessel and on the other hand to be able to begin fabrication without delay.

EXAMPLES:

The contents of N,N-phthaloylaminocaproic acid (PAC), phthalic acid and ε-caprolactam are determined by reversed phase HPLC. The residual water quantities are determined by the Karl Fischer method. The percentages denote percent by weight.

Example 1

1 kg of N,N-phthaloylaminocaproic acid (PAC) having the analytical data:

| PAC: | 93.5% |
|---|---|
| phthalic acid: | 1.45% |
| ε-caprolactam: | 0.55% |
| water: | 4.40% | is heated in a flask to 155° C. As soon as this temperature is reached, a weak vacuum of 105 mbar is applied and the melt is held at this temperature for 5 hours. Samples are taken from the melt after every hour and the sample contents of PAC, phthalic acid, ε-caprolactam and water are determined (Table 1). An undiscolored purified end product is obtained.

TABLE 1

| Sampling at: | PAC* | Phthalic acid* | ε-Caprolactam* | Water* |
|---|---|---|---|---|
| 0 h | 93.50% | 1.45% | 0.55% | 4.40% |

TABLE 1-continued

| Sampling at: | PAC* | Phthalic acid* | ε-Caprolactam* | Water* |
|---|---|---|---|---|
| (Initial value) | | | | |
| 1 h | 97.60% | 1.06% | 0.42% | 0.10% |
| 2 h | 97.86% | 0.66% | 0.35% | 0.05% |
| 3 h | 98.95% | 0.39% | 0.28% | 0.04% |
| 4 h | 98.90% | 0.12% | 0.22% | 0.06% |
| 5 h | 99.45% | 0.09% | 0.18% | 0.05% |

(*Duplicate determinations)

Example 2

1 kg of PAC having the following analytical data:

| PAC: | 94.1% |
|---|---|
| phthalic acid: | 1.26% |
| ε-caprolactam: | 0.50% |
| water: | 4.10% | is heated in a flask to 170° C. As soon as the temperature is reached, a vacuum of 25 mbar is applied and the melt is held at this temperature for 3 hours. Samples are taken from the melt after every half hour or hour, and the sample contents of PAC, phthalic acid, ε-caprolactam and water are determined (Table 2). An almost white purified end product is obtained.

TABLE 2

| Sampling at: | PAC* | Phthalic acid* | ε-Caprolactam* | Water* |
|---|---|---|---|---|
| 0 h (Initial value) | 94.10% | 1.26% | 0.50% | 4.10% |
| 0.5 h | 98.27% | 1.06% | 0.40% | 0.21% |
| 1 h | 98.62% | 0.89% | 0.32% | 0.10% |
| 1.5 h | 98.95% | 0.68% | 0.23% | 0.07% |
| 2 h | 99.34% | 0.33% | 0.18% | 0.08% |
| 3 h | 99.55% | 0.18% | 0.15% | 0.04% |

*Duplicate determinations

Example 3

2 kg of PAC having the following analytical data:

| PAC: | 94.10% |
|---|---|
| phthalic acid: | 1.45% |
| water: | 4.40% | are blanketed with nitrogen in a flask and heated to 155° C. As soon as the temperature is reached, a gentle nitrogen stream (2–10 l/h) is passed over the product melted in the meantime. After every 15 or 30 minutes, samples are taken and analyzed for their contents of PAC, phthalic acid and water (Table 3). A dehydrated PAC is obtained as end product.

TABLE 3

| Sampling at: | PAC* | Water Content* | Phthalic acid* |
|---|---|---|---|
| 0 min | 94.1% | 4.40% | 1.45% |

TABLE 3-continued

| Sampling at: | PAC* | Water Content* | Phthalic acid* |
|---|---|---|---|
| (Initial value) | | | |
| 15 min | 97.32% | 1.15% | 1.38% |
| 30 min | 98.13% | 0.35% | 1.32% |
| 60 min | 98.29% | 0.10% | 1.19% |
| 90 min | 98.76% | 0.12% | 1.04% |
| 120 min | 98.90% | 0.10% | 0.92% |
| 150 min | 98.96% | 0.15% | 0.82% |
| 180 min | 99.01% | 0.0% | 0.85% |

*Duplicate determinations

Example 4

45.2 kg of ε-caprolactam, 59.2 kg of phthalic anhydride and 7.2 kg of deionized water are initially introduced into a 350 l tank having a stirrer. The tank is evacuated twice, treated with nitrogen and sealed pressure-tightly. After heating without stirring, the reaction is carried out with stirring at 155° C. After a reaction time of 10 hours, the steam overpressure is released to atmosphere via a valve. The valve is closed again and the tank is treated again with nitrogen. As soon as a super atmospheric pressure of 5–6 bar has built up, pressure is again released to the atmosphere. After a further repetition of this procedure, the tank is cooled to 120° C. and the product discharged via a flaking roller. The end product obtained is PAC in the form of white flakes.

| Analytical data: | PAC: | 96.34% |
|---|---|---|
| | phthalic acid: | 1.33% |
| | water: | 1.45% |

Example 5 (comparison to Example 4)

45.2 kg of ε-caprolactam, 59.2 kg of phthalic anhydride and 7.2 kg of deionized water are initially introduced into a 350 l tank having a stirrer. The tank is evacuated twice, treated with nitrogen and sealed pressure-tightly. After heating without stirring, the reaction is carried out with stirring at 155° C., the internal pressure increasing to a maximum of approximately 7.5 bar. After a reaction time of 10 hours, the tank is cooled to 120° C. and the product is discharged via a flaking roller. PAC 15 is obtained as white flakes.

| Analytical data: | PAC: | 93.3% |
|---|---|---|
| | phthalic acid: | 1.45% |
| | water: | 5.0% |

The examples clearly show how a crude product of the imidocarboxylic acid PAC can be simply and efficiently purified.

Thus, in Example 1, the content of phthalic acid is reduced by 94% by applying only a weak vacuum, and ε-caprolactam is reduced by almost 70%. The residual water is virtually completely removed. The drying of the crude product PAC is accomplished still more simply by passing a stream of nitrogen over the product melt or repeated "venting/gas treatment" of the reactor space above the product melt (Example 3, 4). In this case, the imidocarboxylic acid PAC is obtained almost anhydrous in the course of 30 minutes or a 70% reduction in the water content is obtained after only threefold "venting/gas treatment". The phthalic acid content can at any rate be reduced by more than 40% by passing over a stream of nitrogen.

I claim:

1. A process for the preparation of purified phthalimidoalkanecarboxylic acids from previously prepared, contaminated phthalimidoalkanecarboxylic acids which are contaminated with phthalic acid, lactam, water or a mixture thereof, including the following steps:
   a) fusing the previously prepared, contaminated phthalimidoalkanecarboxylic acid to obtain a melt,
   b) holding the melt for a period and at a temperature sufficient to cause the phthalic acid, lactam, water, or mixture thereof to substantially separate from the melt, and
   c) cooling the resulting purified product melt.

2. The process as claimed in claim 1, wherein in step a) the thus-obtained melt temperature is between 110° and 200° C.

3. The process as claimed in claim 1, wherein in step a) the thus-obtained melt temperature is between 130° and 170° C.

4. The process as claimed in claim 1, wherein the fusion in step a) is carried out under treatment with an inert gas.

5. The process as claimed in claim 1, wherein the melt in step b) is held under an inert gas at reduced inert gas pressure.

6. The process as claimed in claim 5, wherein the inert gas pressure is between 0.1 and 300 mbar.

7. The process as claimed in claim 5, wherein the inert gas pressure is between 1 and 140 mbar.

8. The process as claimed in claim 5, wherein the inert gas pressure is between 4 and 95 mbar.

9. The process as claimed in claim 1 wherein the period of said step b) is up to 5 hours.

10. The process as claimed in claim 1, comprising:
    prior to said fusing step, treating said contaminated phthalimidoalkanecarboxylic acid with an inert gas in pressure-tight equipment;
    carrying out said fusing step in said pressure-tight equipment zone, the heat applied for said fusing step resulting in the formation of superatmospheric pressure;
    carrying out said step b) with release of said superatmospheric pressure;
    re-introducing inert gas and again forming superatmospheric pressure, followed by release of the superatmospheric pressure thus re-established; and
    repeating said re-introducing and release steps until no superatmospheric pressure is formed.

11. The process as claimed in claim 1, wherein in step a) the contaminated phthalimidoalkanecarboxylic acid is treated with an inert gas and is simultaneously or subsequently melted and in step b) the melt is treated with an inert gas.

12. The process as claimed in claim 11, wherein the gas treatment is carried out by passing an inert gas stream over the melt.

13. The process as claimed in claim 12, wherein the flow rate of the inert gas is 0.1 to 50 l/h.

14. The process as claimed in claim 12, wherein the flow rate of the inert gas is 1 to 30 l/h.

15. The process as claimed in claim 12, wherein the flow rate of the inert gas is 2 to 20 l/h.

16. The process as claimed in claim 12, wherein the inert gas is passed over the melt at atmospheric pressure or at reduced pressure.

17. The process as claimed in claim 16, wherein the reduced pressure is in the range of 500–800 mbar.

18. The process as claimed in claim 12, wherein the inert gas stream is passed over the melt for a period of 0.1 to 6 hours.

19. The process as claimed in claim 12, wherein the inert gas stream is passed over the melt for a period of 0.3 to 3 hours.

20. The process as claimed in claim 12, wherein the inert gas stream is passed over the melt for a period of 0.5 to 1.5 hours.

21. The process as claimed in claim 1, wherein in step c) the purified product melt is cooled to or immediately above the solidification point.

* * * * *